United States Patent [19]

Bedard et al.

[11] Patent Number: 4,764,760

[45] Date of Patent: Aug. 16, 1988

[54] AUTOMATIC GAIN CONTROL FOR MACHINE TOOL MONITOR

[75] Inventors: James F. Bedard, Schenectady; Walter Whipple, III, Amsterdam, both of N.Y.

[73] Assignee: General Electric Company, Schenectady, N.Y.

[21] Appl. No.: 943,397

[22] Filed: Dec. 19, 1986

[51] Int. Cl.[4] .............................................. G08B 21/00
[52] U.S. Cl. .................................... 340/680; 340/683; 73/104; 73/660; 364/474
[58] Field of Search ........................ 340/683, 680, 679; 73/104, 660, 658; 364/474, 475, 508; 330/284

[56] References Cited

U.S. PATENT DOCUMENTS

| | | | |
|---|---|---|---|
| 4,514,797 | 4/1985 | Begin | 364/148 |
| 4,563,897 | 1/1986 | Moore | 73/587 |
| 4,724,524 | 2/1988 | Thomas et al. | 340/680 X |

OTHER PUBLICATIONS

S. R. Hayashi et al., "Automatic Tool Touch and Breakage Detection in Turning", Intl. Congress of Metalworking and Automation, Hanover, Sep. 18-19, 1985, pp. 96-101.

*Primary Examiner*—Joseph A. Orsino
*Assistant Examiner*—Jeffery A. Hofsass
*Attorney, Agent, or Firm*—Donald R. Campbell; James C. Davis, Jr.; Paul R. Webb, II

[57] ABSTRACT

An acoustic tool break detector monitors vibration caused by a cutting process and has an analog amplifier to condition the signal, then searches for a rapid sustained change in signal level indicative of a cutting tool break. An automatic gain control circuit dynamically controls the gain of the analog amplifier and adjusts the output cutting noise signal to a desired average level during an active cut while allowing use of such a break algorithm. The time rate at which the AGC changes gain is constant and independent of gain; it is set such that a gain change of 2:1, for instance, takes longer than the confirmation period for a tool break. The analog amplifier has a variable attenuator whose gain is set by the outputs of an up/down counter; these outputs are fed back to a variable clock whose rate is dependent on gain at any instant. The clock outputs drive the counter until the analog cutting noise signal is within a preselected window.

14 Claims, 8 Drawing Sheets

ANALOG CHANNEL OUTPUT SIGNAL

AUTOMATIC GAIN CONTROL FOR MACHINE TOOL MONITOR

BACKGROUND OF THE INVENTION

This invention relates to an acoustic tool break detection system and method to automatically adjust the cutting vibration signal to a desired average during a machining operation while detecting a broken tool by monitoring the cutting signal.

A machine tool monitor (MTM) which interprets vibration signals generated by the interaction of a cutting tool with a workpiece, and serves as a tool touch and tool break detector, is described in several commonly assigned copending applications and in published papers such as "Automatic Tool Touch and Breakage Detection in Turning", S. R. Hayashi et al, ICMA, Hanover, West Germany, Sept. 18–19, 1985. The MTM is comprised of a vibration sensor such as an accelerometer, an analog channel with amplification and signal preprocessing, an analog-to-digital converter, and a microprocessor with associated digital hardware. The accelerometer typically has a broadband response which the analog channel bandpass filter restricts. The gain stage keeps signals within the dynamic range of the system, and an energy detector is provided consisting of a full wave rectifier and low pass anti-aliasing filter. In one analog preprocessor the accelerometer output signal is conditioned to a 0 to 10 volt dc 500 Hz signal for input to the digital processor. An algorithm analyzes this signal to determine if a tool break has occurred by looking for a rapid sustained change in a signal level. It is desirable to maintain the average A/D converter input level at approximately one volt for dynamic range considerations. This means that the gain of the analog amplifier must be set every time a level change is expected due to a process cutting change such as depth of cut or different tool-workpiece combinations.

As set forth in copending application Ser. No. 744,083, filed June 12, 1985 now U.S. Pat. No. 4,724,524, C. E. Thomas et al, "Vibration-Sensing Tool Break and Touch Detector Optimized for Machining Conditions", the analog channel gain control is comprised of a multiplying digital-to-analog converter used as a variable attenuator whose gain is adjusted by setting its binary inputs via a signal from the digital hardware. The desired gain may be calculated in the MTM from machining parameters transferred from the part program, and alternatively the desired gain is programmed as part of the parts program. The gain change can be done by the part programmer through part programming additions or manually by switch settings; eliminating this operation unloads the programmer from extra code generation. There is also a problem in that a cutting process does not necessarily produce a constant signal level. The signal can change over the full 10 volt range during a process, for a gain setting that produces a one volt average for the majority of the operation. It is desirable to minimize this variation without affecting the rapid sustained level changes indicative of a tool break.

U.S. Pat. No. 4,514,797 is relevant and discloses a software-controlled automatic gain control (AGC) for a worn cutting tool detector.

SUMMARY OF THE INVENTION

An object of this invention is to provide a hardware AGC to dynamically control the gain of the analog channel of a machine tool monitor so that there is substantially no alteration of the preprocessed vibration signal for the time period required by tool break signal pattern recognition logic to detect an abruptly occurring break.

Another object is to provide the foregoing system with attributes including one or more of the following: holding gain to a preset value until a cutting signal is present, maintaining average cutting signal at a selected level during the cutting operation, preventing reset of gain during certain unique process situations such as runout, when the signal falls to zero, yet recognize end of cut zero level so gain may be reset, and minimizing human interaction for setting of preset gain and provide adequate response to allow one preset gain set for a large range of cutting conditions.

Yet another object is the provision in the tool break detection system of a dead band around a desired average analog channel output voltage level to minimize hunting.

The improved tool break detection system is comprised of a vibration sensor, an analog channel to condition the signal to a low dc output voltage in a restricted frequency range and that has a variable attenuator to control gain, and a digital processor as just described. An automatic gain control means dynamically controls the gain of the variable attenuator and adjusts the dc analog output voltage to a designated average level in such manner that the time rate at which gain changes is constant and independent of gain and there is no significant change in signal level during the confirmation time period to detect a tool break of the type that results in a rapid sustained change in cutting noise. The variable attenuator may be a multiplying digital-to-analog converter (MDAC) and the AGC circuit includes an up-/down counter whose outputs set the MDAC gain and are also fed to a variable clock to generate clock pulses for the counter at a variable rate which is a function of gain at any instant. The clock output drives the counter until the analog channel output signal level is within a window about the desired average level or the counter reaches maximum or minimum count.

Other features of the AGC circuit are a level detecting means which generates a count up or count down signal when the detected analog output voltage is at preselected levels below or above the desired average level; one of these signals is presented to the counter to determine whether it increments or decrements. Inhibit means are provided to inhibit the variable clock if the detected voltage is in the window between preselected levels. The level detector further checks for a threshold voltage and, if below, sends a signal to a timer and, after a given delay, enables means to preset the counter to yield the preset gain. This threshold keeps gain at the preset level between cuts. The threshold voltage is above the machine tool background noise level, and the timeout period before presetting gain is long enough that the counter is not preset during normal cutting operations that produce intermittent zero or below-threshold cutting signals. The preset gain may have a constant value or may vary from cut to cut depending on cutting conditions and reduce the need for AGC action.

Another aspect of the invention is a method of detecting a cutting tool break comprised of generating a vibration signal and preprocessing it in an analog amplifier and signal processing channel to yield an analog cutting noise signal. The latter is analyzed to detect a tool break acoustic signature characterized by a rapid and substantial cutting signal change which is sustained for a confirmation period, typically about one second. The gain of the analog amplifier is controlled to adjust the analog cutting signal to a designated signal level within a window and so that the time rate of gain change is substantially constant and a preselected ratio of gain change, say 2:1, takes longer than, and up to several times longer than, the confirmation period.

DETAILED DESCRIPTION OF THE INVENTION

Figure 1:
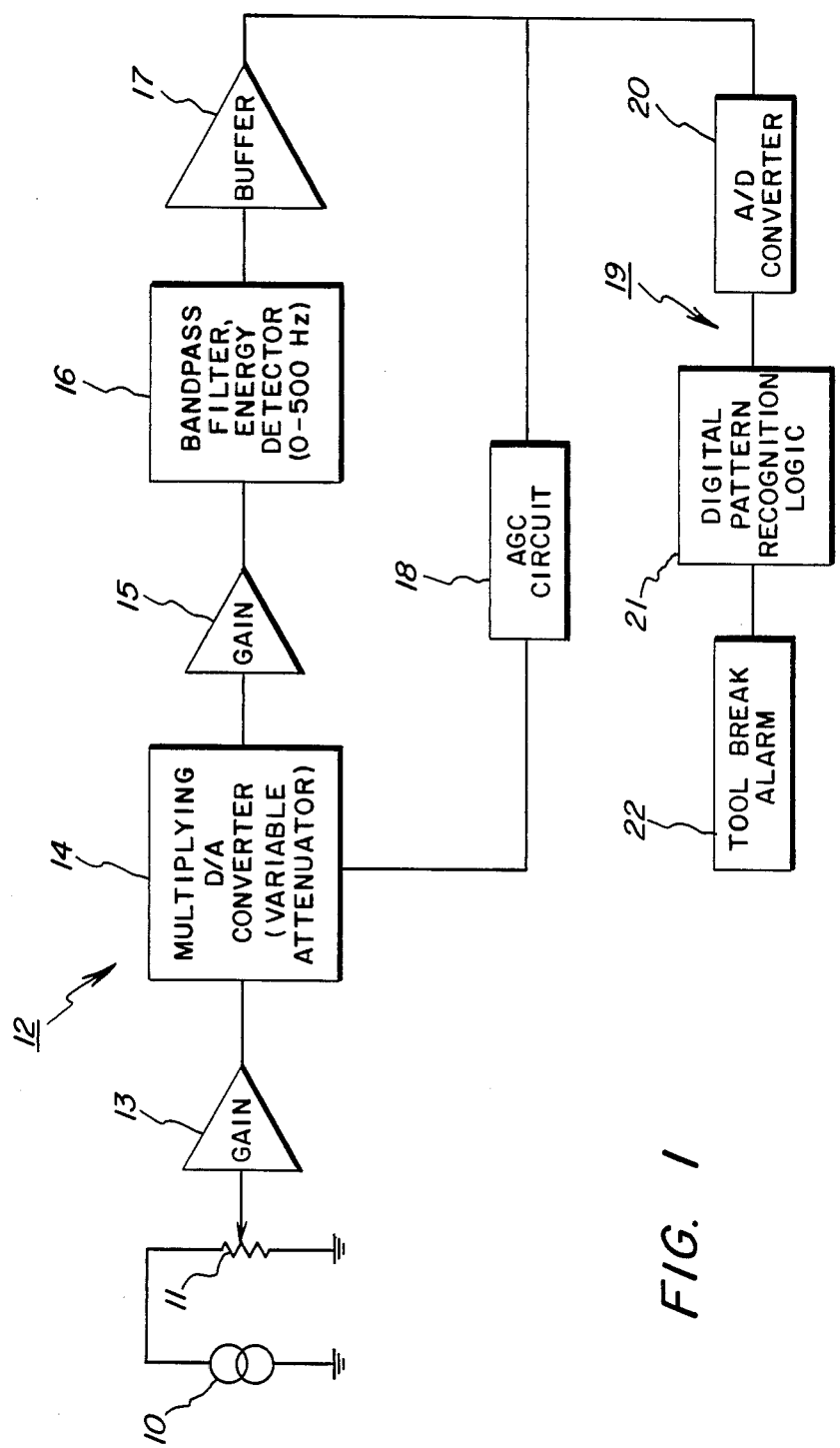
FIG. 1 is a block diagram of a machine tool monitor to detect broken cutting tools which has an automatic gain control in the analog signal processing channel.

Referring to FIG. 1, the machine tool monitor comprises a vibration sensor such as an accelerometer 10 which is mounted on the machine tool, for instance a lathe or milling machine, in a location with good coupling to vibrations generated by the interaction of a cutting tool with a workpiece. The output of one accelerometer is a low level AC analog signal with frequency content between approximately 0–70 KHz, and amplitude that varies with the strength of the vibrations caused by the cutting process. An input potentiometer 11 matches the dynamic range of the electronics to the accelerometer. An analog signal processing channel 12 conditions this signal to a low dc voltage in a restricted frequency range and prepares it for analog-to-digital conversion. An analog amplifier has a fixed gain section 13, a variable attenuator such as multiplying digital-to-analog converter 14, and a fixed gain section 15. Band pass filtering and "envelope" or energy detection are performed at 16. Lower frequency machining noise below 30 KHz is filtered out and the machine tool monitor does not use frequencies above 100 KHz as they are strongly attenuated unless the sensor is close to the tool holder. The energy detector is comprised of a full wave rectifier and a 500 Hz or less anti-aliasing filter. The analog cutting noise output signal is presented to a buffer 17 and typically is a 0 to 10 volt, dc to 500 Hz bandwidth signal.

For dynamic range considerations it is desirable to maintain the average analog channel output voltage to approximately one volt for the reasons already given; AGC circuit 18 does this while allowing the present tool break algorithm to be used without modification. The gain of variable attenuator 14 is adjusted by the AGC circuit in such manner that the rate of gain change is a function of the gain at any instant.

Figure 2:
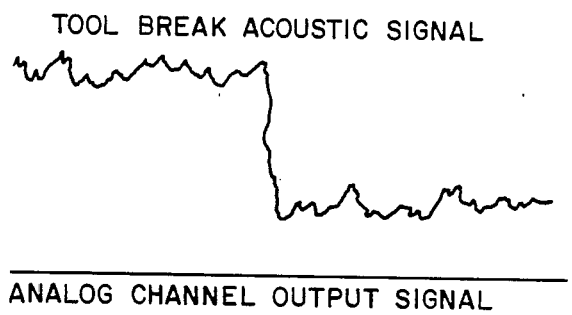
FIG. 2 shows one tool break acoustic signature, a rapid, substantial, sustained drop in the processed vibration signal level.
Figure 3:
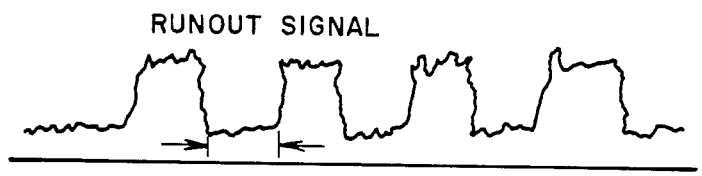
FIG. 3 illustrates a vibration signal from intermittent cutting on a rough surface which does not trigger the tool break alarm.

The first part of digital processor 19 is an analog-to-digital converter 20 which samples and digitizes the analog channel output waveform. Digital pattern recognition logic 21 generates a tool break alarm 22 whenever it detects a tool break acoustic signature characteristic of a significant tool break event that is likely to damage the tool or workpiece or force a re-cut. The vibration signature of one type of abruptly occurring major tool break is shown in FIG. 2. The running mean signal level of a chosen number of samples of the cutting noise signal is calculated, and a rapid, substantial, sustained change in mean signal level, either an increase or decrease, that persists for longer than a set confirmation period is indicative of a tool break. One common normal cutting signal that this break detection logic ignores is shown in FIG. 3, a runout signal produced at the start of a cut during rough surface cutting, when there is alternate metal-cutting and air-cutting. There is a rapid and substantial change in signal level but the high level signal duration is shorter than a workpiece revolution and is not sustained long enough to satisfy the confirmation test.

Figure 4:
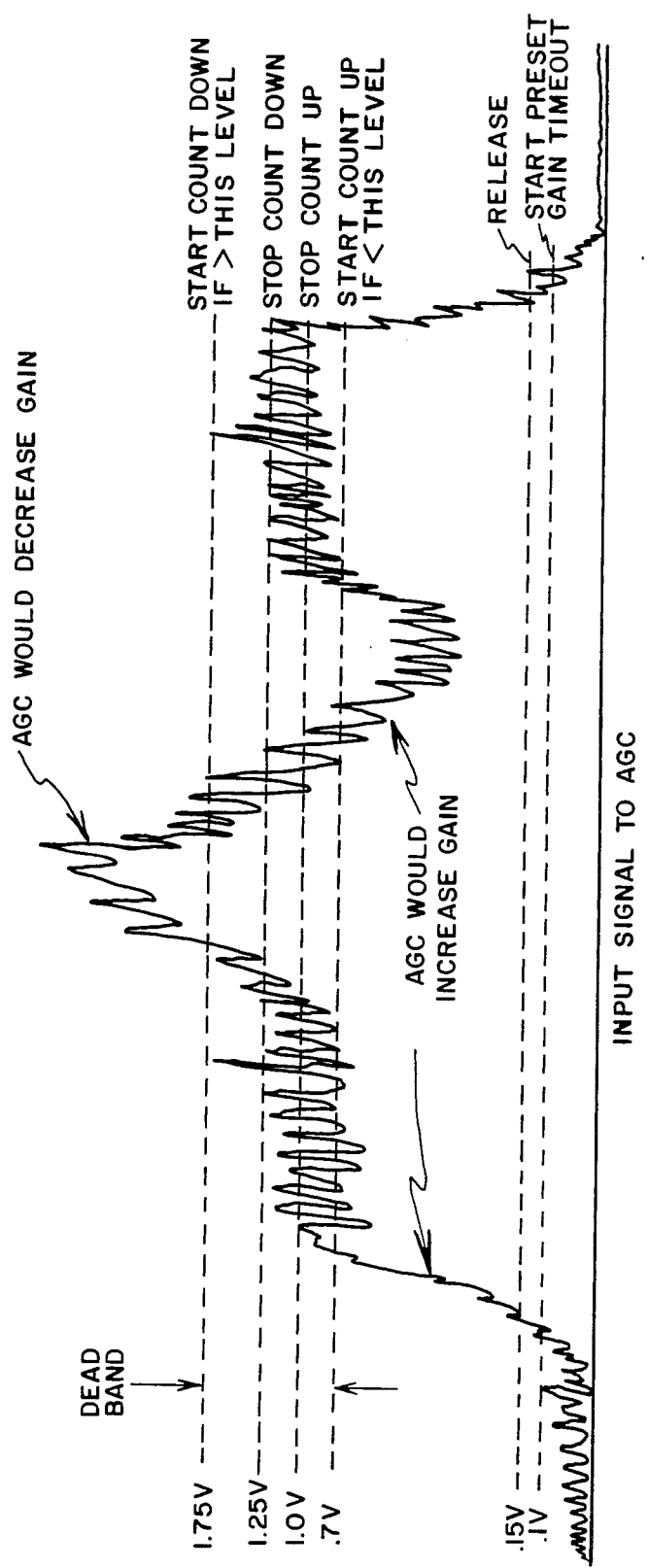
FIG. 4 illustrates the action of the AGC as a function of the input signal level.

The action of AGC circuit 18 as a function of the input signal level at the analog channel output is illustrated in FIG. 4. The voltages at the left at which various actions are taken are for one application of the MTM and may vary from these figures for another application. The count down and count up commands at the right refer to up/down counter 23 in FIG. 5; counting down decreases the analog amplifier gain and counting up increases the gain. The 0.15 v threshold voltage to release the AGC is above the machine tool background noise level. An analog cutting signal level between 0.15 v and 0.7 v is below the desired average level of 1 v and the AGC would increase gain. Count up will occur in this range and stop at 1 v. A signal level between 1.75 v and 10 v causes the AGC to decrease gain; count down starts at levels above 1.75 v and stops at 1.25 v. There is a dead band or window between 0.7 v and 1.75 v where no action is taken by the AGC. The two hysteresis bands are 0.7 v–1 v and 1.75 v −1.25 v. The hysteresis at 0.15 v and 0.1 v controls the AGC on and preset timeout signal levels. The 0.15 v AGC release level works on rising signals such as at the start of a cut. The 0.1 v AGC hold level is activated by falling signals such as at the end of a cut. If the signal falls below the 0.1 v level the AGC is inhibited and if it stays below for a preset delay time, longer than that of a run out period, the gain is automatically preset to the initial value it was set to at the start.

Figure 5:
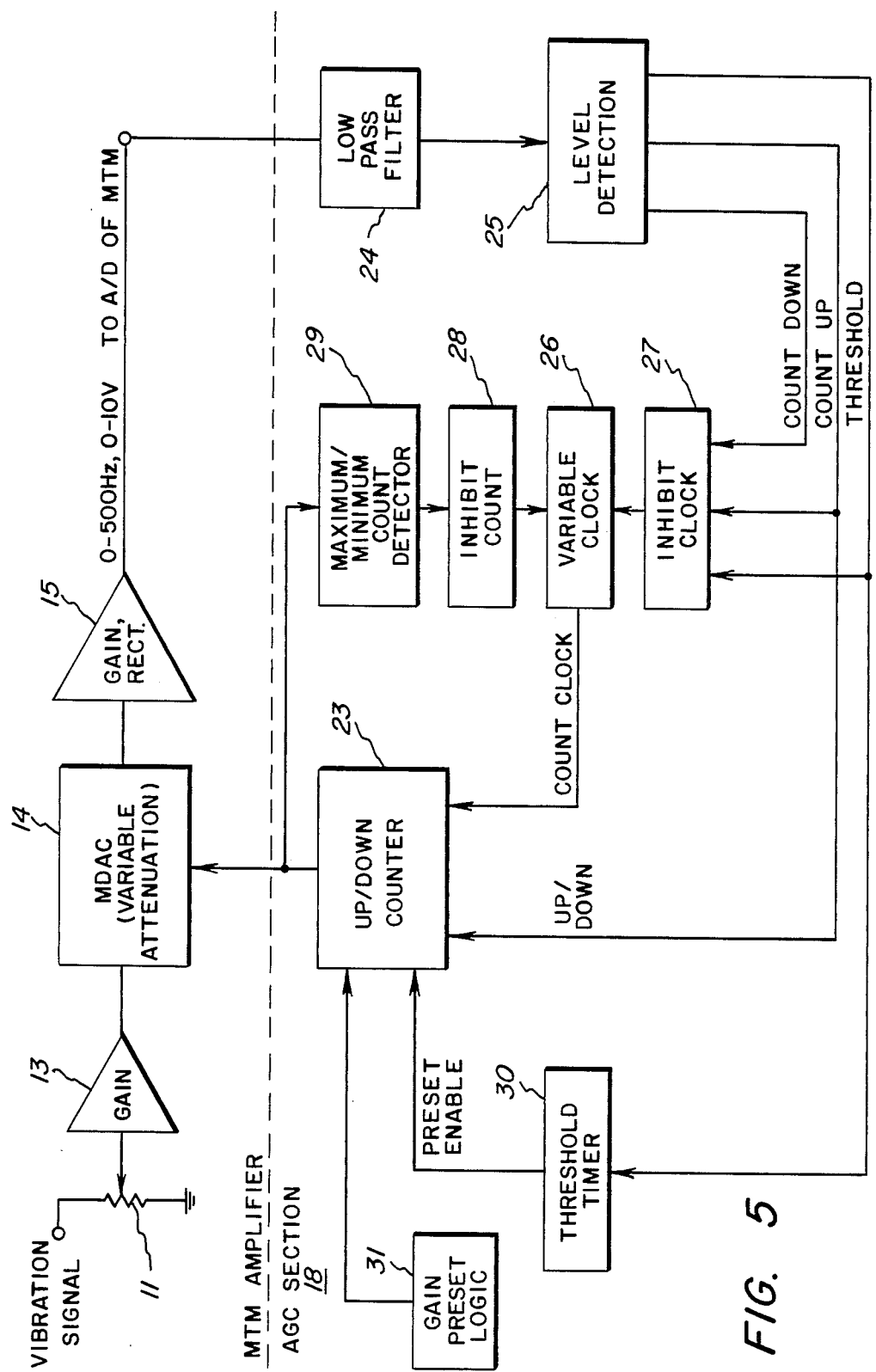
FIG. 5 is a block diagram of the digital automatic gain control and analog amplifier.

FIG. 5 is a block diagram of automatic gain control circuit 18 and the machine tool monitor analog amplifier of FIG. 1. Device 15 represents both the fixed gain and rectification functions. The gain of digitally programmable multiplying digital-to-analog converter 14 is adjusted by setting its binary inputs via signals from the parallel outputs of an up/down counter 23, determining the gain of the analog amplifier channel. The MDAC 14 can produce a relative gain factor of any integer from 1 to 1023, in accordance with the digital control signals it receives from counter 23. AGC section 18 is comprised of an input low pass filter 24 and level detection circuit 25; a variable clock 26 to generate clock pulses at a rate dependent on the counter outputs and the current analog amplifier gain, and inhibit clock and inhibit count circuitry 27 and 28; a maximum/minimum count detector 29; the presettable up/down counter 23; a threshold timer 30; and gain preset logic 31 for the counter. The dc to 500 Hz output signal of the analog amplifier channel is input to the AGC section through a 100 Hz low pass filter 24 which provides initial signal averaging. This signal is then applied to the level detector 25 which provides three control signals -count up, count down, and threshold. The threshold signal is used to hold off AGC action when the signal is below a selected level. If the signal is below threshold for a time, about 1 second, set by the threshold timer 30, a signal to the preset enable input of up/down counter 23 permits the preset logic 31 to set counter 23 to a given count and force the gain of MDAC 14 to a preset value. A preset gain of 50 may be selected, for example. The delay imposed by timer 30 is longer than the duration of the below-threshold or zero signal level (between the arrows in FIG. 3) portion of, a runout signal. On the other hand, an end of cut zero level is recognized so gain may be reset.

Figure 6:
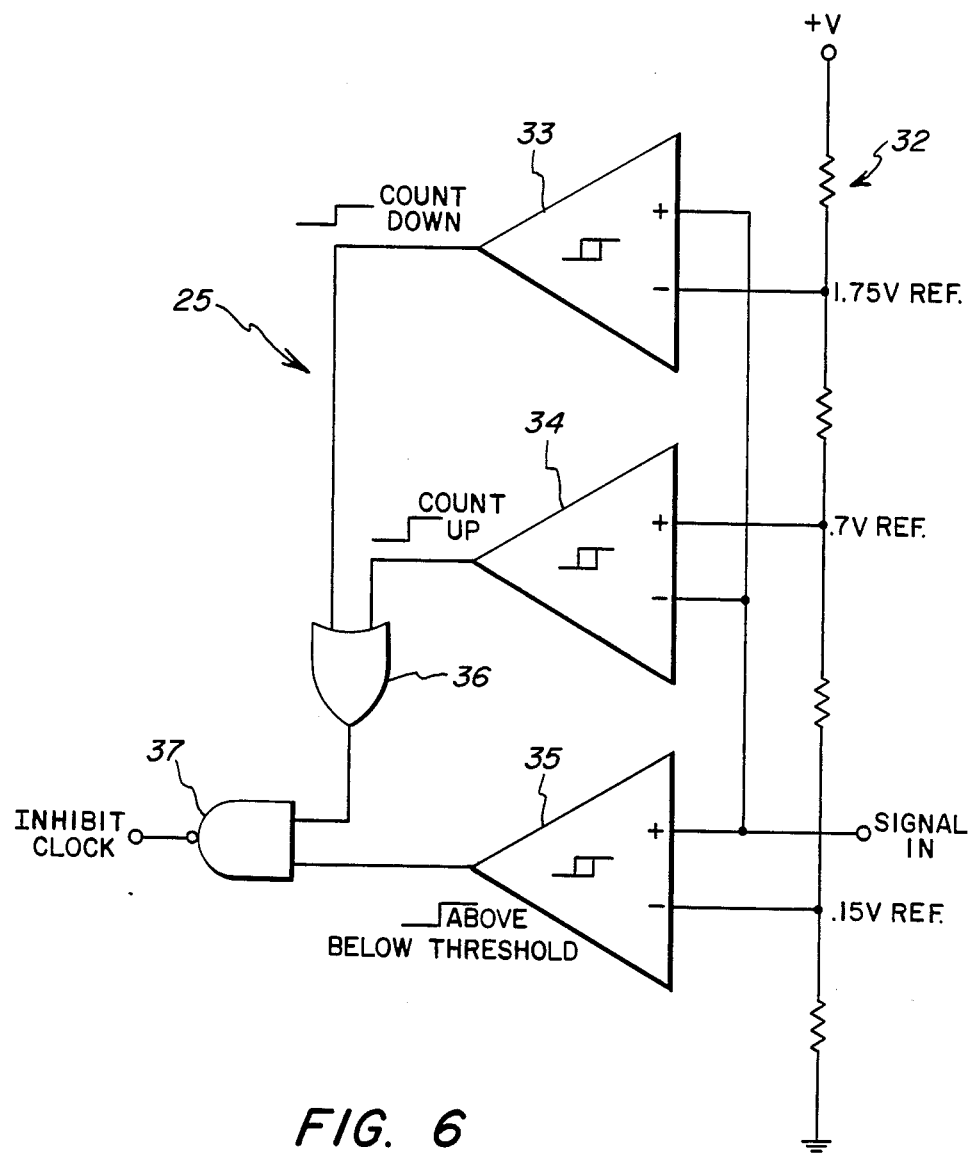
FIG. 6 is a simplified diagram of the level detection circuit.

Level detection circuit 25 is shown in more detail in FIG. 6. A resistor voltage divider 32 provides three reference voltages: 1.75 v, 0.7 v, and 0.15 v. These are fed to the inverting, noninverting, and inverting inputs of three comparators 33, 34 and 35, all of which have hysteresis characteristics. The filtered analog channel output signal is presented to the other input of each comparator. The first produces a count down signal if the analog cutting signal level is higher than 1.75 v, and the second a count up signal when that voltage is below 0.7 v. The third device 35 compares the analog cutting signal to the 0.15 v threshold voltage and outputs an above threshold signal if it is higher. The count down and count up signals are presented to an OR circuit 36 which has a true output if either is present. This is one input to NAND circuit 37, the other being the above threshold signal. Variable clock 26 is inhibited if the input signal level to the AGC is below threshold; the variable clock is enabled if there is an above threshold signal and either a count up or count down signal. The variable clock is also inhibited when there is an above threshold signal but neither a count up or count down signal because the input signal is within the window between 0.7 v and 1.75 v. The count up signal is fed to the up/down input of counter 23 to set the direction of counting when a count clock is received.

The variable clock 26 is essential to allow the MTM abrupt tool break algorithm to work without modification from its original design. For more information on the latter refer to allowed applications Ser. Nos. 664,188 and 664,189, filed Oct. 24, 1984, now U.S. Pat. Nos. 4,636,780 and 4,636,779 both C. E. Thomas et al, the disclosures of which are incorporated herein by reference. If a rapid change of instantaneous signal level compared to the running mean is detected meeting selectable criterion, currently a 0.5 decrease or a two times increase, the level is then checked to see if it maintains the change for a determinable confirmation period, currently up to 0.625 seconds. If it does, a break alarm is given. It is therefore imperative that the AGC response does not alter the signal level significantly within this confirmation period so that the present algorithm may still be used for break recognition. If a constant frequency clock were used to drive the counter 23, the rate of change of gain would vary with gain since one clock period=one count. Therefore, low gain determines the clock frequency to meet a 0.5 level change criteria, i.e. a gain change from 1 to 2 or vice versa must not occur in less than 0.625 seconds. Thus this would be the clock period. However, at high gain, this rate of change makes the AGC action very sluggish—the same gain change ratio at a gain of 512 would mean counting down to 256, at a time of 160 seconds (256 counts times 0.625 second/count), much too slow to be useful. This problem is averted by having the AGC change gain at a substantially constant rate such that a 2:1 gain change from 512 to 256 takes the same time as one from 24 to 12. The time rate at which the AGC changes gain is constant and independent of gain; it is set such that a gain change of 2:1 takes longer than the confirmation period for a tool break.

Figure 7:
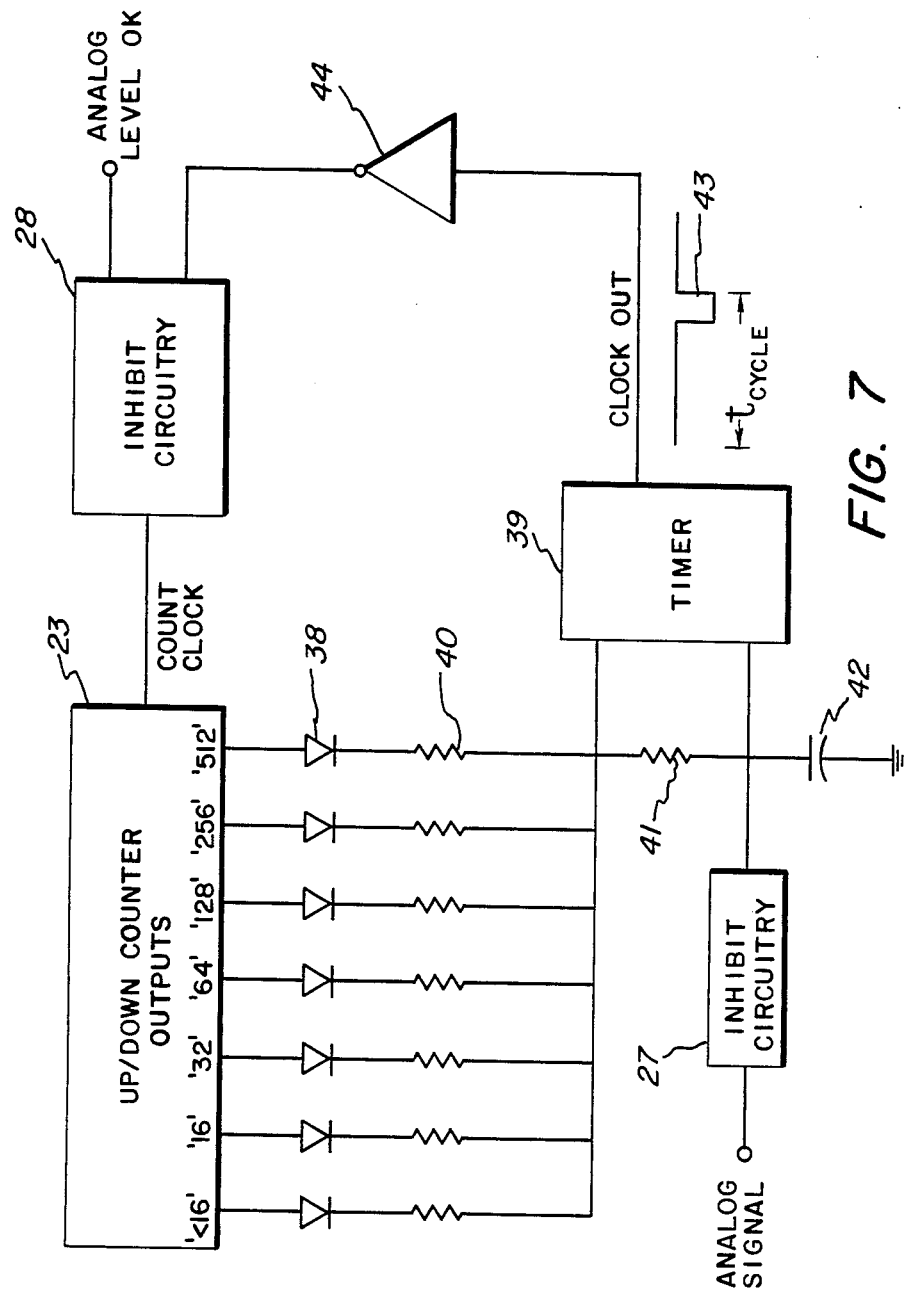
FIG. 7 illustrates the variable clock driven by outputs of the up/down counter which controls the multiplying digital-to-analog converter.

Turning to FIG. 7, this is accomplished by the use of a binary weighted oscillator. Only seven of the binary related counter outputs are utilized and the three lowest bits are not used. The variable clock output changes at discrete steps of sixteen counts. The binary outputs of up/down counter 23 are connected through isolation diodes 38 to provide the drive to the timing resistors of an astable oscillator utilizing a suitable timer 39. Seven timing resistors 40 are respectively in parallel and each is in series with a resistor 41 and timing capacitor 42. The oscillator frequency is determined by the capacitor and the sum of the timing resistor(s) and resistor 41. Resistor 41 sets the period of output clock pulse 43 to a small fraction of the timing cycle so that it does not affect the timing. Inhibit circuitry 27 assures that the first count is always a full cycle time by keeping the timing capacitor 42 discharged. The inhibit clock signal turns on a transistor (not shown) which discharges the capacitor. Clock output pulses 43 are inverted at 44 and fed to the count clock input of up/down counter 23 unless inhibited by the inhibit count circuitry 28. The clock output, whose rate is dependent upon the counter outputs, drives the counter until the signal level at the analog channel output is within the desired window or the counter reaches maximum or minimum output. When this occurs, the clock is inhibited.

Figure 8:
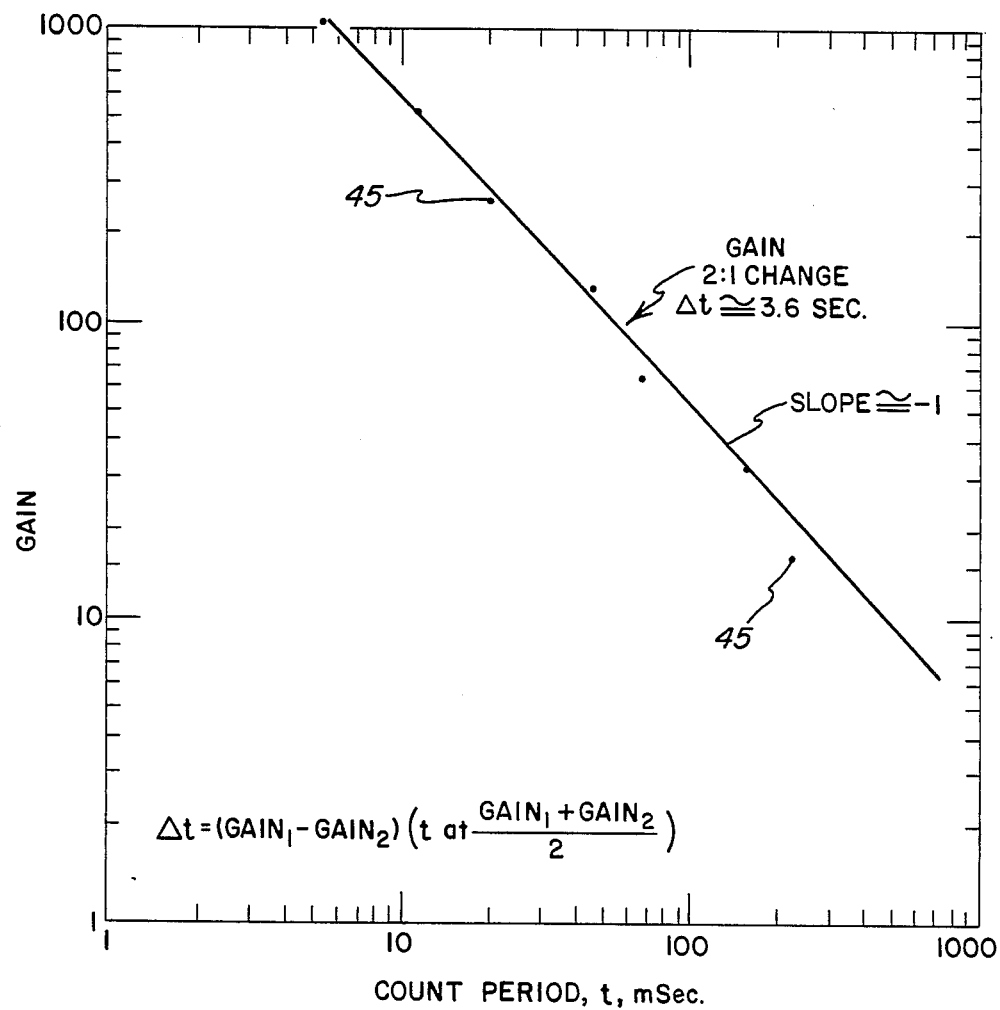
FIG. 8 shows, on a log-log scale, gain versus the count period of generated clock counts.

One variable clock has the following components: timing resistors 40, from left to right, are 1.5M, 680K, 470K, 240K, 130K, 62K and 32K, and resistor 41 is 510 ohms and timing capacitor 42 is 0.47 $\mu f$. The clock pulse width is 166$\mu$ sec. The calculated cycle time at "16" is 228 msec, at "512" is 11.24 msec, and at "256" is 20.2 msec. FIG. 8 shows the relation of the count period, t, in milliseconds and gain (1 to 1023); the seven calculated points 45 are shown the slope of the curve is approximately $-1$. This curve gives the average timing to obtain a 2:1 change in gain, say from 500 to 250 or 200 to 100, as approximately 3.6 seconds, several times longer than the confirmation period of 0.625 seconds but short enough for effective AGC action. The AGC is maintained for considerably longer than the confirmation period of the break algorithm and there is little effect on the rapid sustained signal level change tool break signature. By appropriate choice of capacitor, the time may be set to the desired value.

Figure 9:
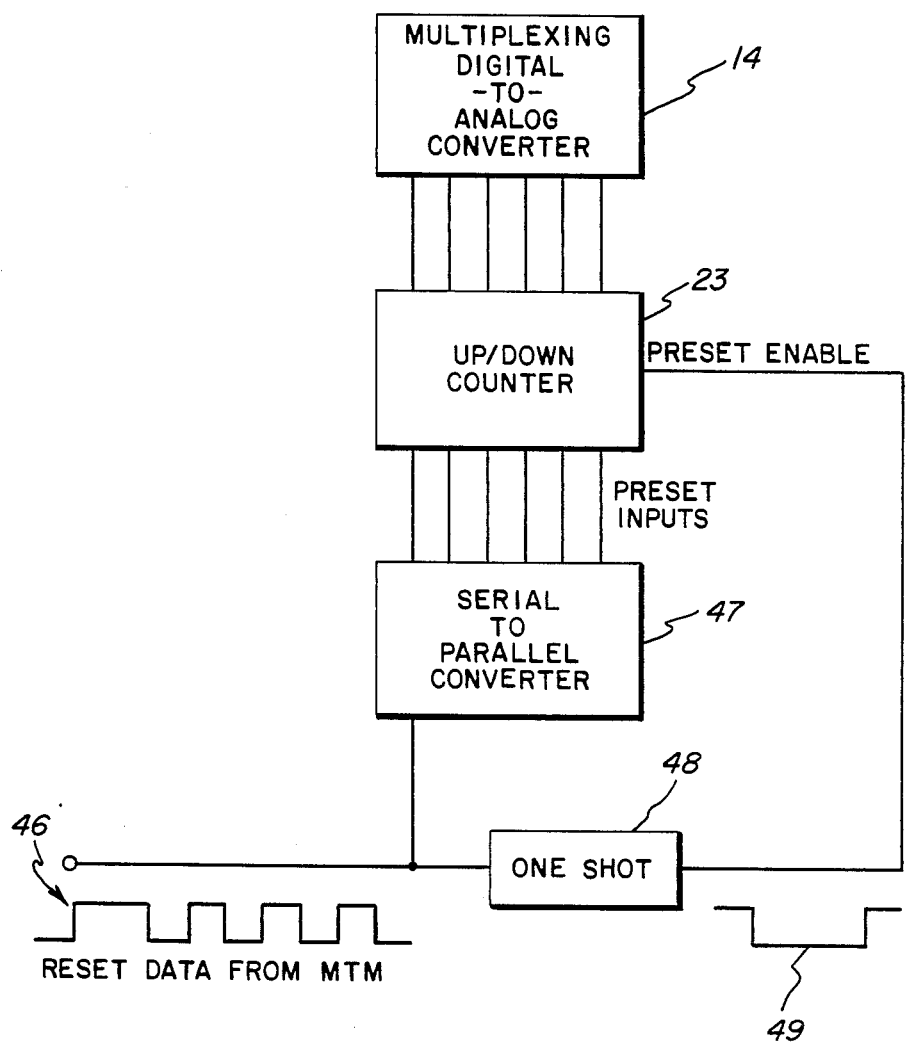
FIG. 9 illustrates one technique to control preset of the counter from the digital processor section.

FIG. 9 illustrates control of preset gain by the machine tool monitor and that preset gain can be varied remotely to initialize the start gain as a function of the cutting conditions expected in the same manner presently used in the MTM, see U.S. Pat. No. 4,724,524. Preset gain is set by the same method—serial data 46 is fed to a serial-to-parallel converter 47 which inputs to the MDAC 14 parallel inputs. The up/down counter 23 is placed between these chips and a one-shot 48 is added to enable preset of the counter until data is entered. Following the end of cut, reset data 46 from the MTM which specifies the preset gain value for the next cut is fed to a serial-to-parallel converter 47 and hence to up/down counter 23. The first bit of the reset data triggers one-shot circuit 48 and the pulse 49 presented to the preset enable input of counter 23 is longer than the reset data stream. The operator can set the gain for whatever value he wants and from his experience on a given cut can make an estimate as to what the average gain is on that cut, say 75 or 150. The AGC circuit takes over from there; gain changes by AGC action are reduced because the preset gain varies from cut to cut.

In conclusion, the method of detecting a tool break which results in an abrupt and significant change in cutting conditions is that the raw sensor signal is preprocessed in an analog channel comprised of an analog amplifier to yield a dc cutting signal and the latter is digitally processed to detect a rapid sustained change in mean signal level which persists for a given confirmation period. The automatic gain control circuit adjusts the analog cutting signal level to a designated level within a window and to have a given ratio of gain change in a substantially constant time longer than, and up to several times longer than, the period to confirm detection of such a major tool break event.

While the invention has been particularly shown and described with reference to preferred embodiments thereof, it will be understood by those skilled in the art that various changes in form and details may be made without departing from the spirit and scope of the invention.

The invention claimed is:

1. In a tool break detection system having a vibration sensor that generates a signal whose amplitude varies with the strength of the vibration caused by a cutting process, an analog channel to condition the sensor signal to a dc output voltage in a restricted frequency range and which has a variable attenuator to control gain, means to sample and digitize said output voltage, and means to detect a rapid change in signal level that is sustained for a given confirmation period and is indicative of a cutting tool break, the improvement comprising:

automatic gain control means to dynamically control the gain of said variable attenuator and adjust said dc output voltage to a designated signal level within a window in such manner that the time rate at which gain changes is constant and independent of gain and there is no significant change in signal level during said confirmation period to detect a tool break.

2. The system of claim 1 wherein said automatic gain control means is comprised of a counter whose outputs determine the gain of said variable attenuator and which are also fed to a variable clock to generate clock pulses for said counter at a variable rate which is a function of the gain at any instant.

3. The system of claim 2 wherein said variable clock is comprised of a binary weighted oscillator connected through isolation means to the outputs of said counter, and a timer which generates said clock pulses.

4. The system of claim 3 further comprising means to inhibit said variable clock upon said counter going above and below predetermined maximum and minimum counts.

5. The system of claim 2 wherein said counter is an up/down counter, and means for level detecting said dc output voltage and determining whether said counter counts up or down and whether said variable clock is to be inhibited.

6. The system of claim 5 wherein said level detecting means generates count up and count down signals when the detected voltage is respectively below and above the window, and one of said last-mentioned signals is presented to said counter to enable count up or count down.

7. The system of claim 6 further comprising means for inhibiting said variable clock when the detected voltage is within the window.

8. The system of claim 6 wherein said level detecting means checks for a threshold voltage and, if the detected level is below, provides a threshold signal to a timer and, after a predetermined delay, enables means to preset said counter to yield a selected preset gain.

9. The system of claim 8 wherein said threshold voltage is above the background noise level of a machine tool on which said cutting tool is mounted, and said predetermined delay is long enough that said counter is not preset during normal cutting operations such as runout that produce an intermittent below-threshold voltage.

10. The system of claim 8 wherein said means to preset gain sets a gain value which depends on cutting conditions and varies from cut to cut.

11. The method of detecting a cutting tool break on a machine tool by monitoring vibrations at the tool-workpiece interface, comprising:

generating a vibration signal which is preprocessed in an analog channel comprised of an analog amplifier and which produces a unidirectional analog cutting noise signal;

digitally processing said cutting signal to detect a tool break acoustic signature of the type having a rapid and substantial change in signal level which is sustained for a given confirmation period; and automatically controlling the gain of said analog amplifier to adjust said analog cutting signal to a designated signal level within a window and so that the time rate of gain change is substantially constant and a preselected ratio of gain change takes longer than said confirmation period to detect a tool break.

12. The method of claim 11 wherein the gain of said analog amplifier is fed back to an automatic gain control circuit and the rate of gain change is a function of the gain at any instant.

13. The method of claim 12 wherein gain is increased upon detecting an analog cutting noise signal higher than a threshold voltage and below said window, and decreased upon detecting a cutting signal higher than said window.

14. The method of claim 13 wherein said threshold voltage is above background noise levels of said machine tool, and the additional step of presetting gain to an assigned value if a below-threshold voltage is sensed for a time exceeding a delay period.

* * * * *